(12) United States Patent
Won et al.

(10) Patent No.: US 9,095,530 B2
(45) Date of Patent: *Aug. 4, 2015

(54) ORAL AND PERSONAL CARE COMPOSITIONS

(75) Inventors: Betty Won, New Brunswick, NJ (US); Paloma Pimenta, Staten Island, NY (US); Shira Pilch, Highland Park, NJ (US); James Masters, Ringoes, NJ (US); Mahmoud Hassan, Somerset, NJ (US); Ben Gu, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/991,993

(22) PCT Filed: Dec. 7, 2010

(86) PCT No.: PCT/US2010/059156
§ 371 (c)(1),
(2), (4) Date: Jun. 6, 2013

(87) PCT Pub. No.: WO2012/078134
PCT Pub. Date: Jun. 14, 2012

(65) Prior Publication Data
US 2013/0251645 A1 Sep. 26, 2013

(51) Int. Cl.
| *A61K 8/86* | (2006.01) |
| *A61K 8/27* | (2006.01) |
| *A61K 8/29* | (2006.01) |
| *A61K 8/73* | (2006.01) |
| *A61Q 11/00* | (2006.01) |

(52) U.S. Cl.
CPC ... *A61K 8/86* (2013.01); *A61K 8/27* (2013.01); *A61K 8/29* (2013.01); *A61K 8/731* (2013.01); *A61Q 11/00* (2013.01)

(58) Field of Classification Search
CPC ........... A61K 8/27; A61K 8/29; A61Q 11/00
See application file for complete search history.

(56) References Cited

U.S. PATENT DOCUMENTS

| 4,022,880 A | 5/1977 | Vinson et al. |
| 4,032,627 A | 6/1977 | Suchan et al. |
| 4,820,506 A | 4/1989 | Kleinberg et al. |
| 4,839,157 A | 6/1989 | Mei-King Ng et al. |
| 5,695,746 A | 12/1997 | Garlick, Jr. et al. |
| 5,948,430 A | 9/1999 | Zerbe et al. |
| 6,135,986 A | 10/2000 | Leisner et al. |
| 6,177,096 B1 | 1/2001 | Zerbe et al. |
| 6,241,974 B1 | 6/2001 | White, Jr. et al. |
| 6,375,933 B1 | 4/2002 | Subramanyam et al. |
| 6,596,298 B2 | 7/2003 | Leung et al. |
| 6,669,929 B1 | 12/2003 | Boyd et al. |
| 7,763,235 B2 | 7/2010 | Boyd et al. |
| 2003/0053962 A1 | 3/2003 | Zerbe et al. |
| 2005/0019273 A1 | 1/2005 | Boyd et al. |
| 2007/0020201 A1 | 1/2007 | Boyd et al. |
| 2008/0014224 A1 | 1/2008 | Boyd et al. |
| 2008/0138369 A1 | 6/2008 | Boyd et al. |
| 2008/0160056 A1 | 7/2008 | Boyd et al. |
| 2012/0042893 A1* | 2/2012 | Campbell et al. ............ 132/200 |
| 2012/0045402 A1* | 2/2012 | Morgan et al. .................. 424/52 |
| 2012/0045495 A1* | 2/2012 | Martinetti et al. ............ 424/401 |

FOREIGN PATENT DOCUMENTS

| WO | WO 2005/058265 | 6/2005 |
| WO | WO 2007/013937 | 2/2007 |
| WO | WO 2007013937 A1 * | 2/2007 |
| WO | WO 2010/138544 | 12/2010 |

OTHER PUBLICATIONS

International Search Report and Written Opinion in International Application No. PCT/US10/059156, mailed Sep. 15, 2011.
Liao et al., 2006, "Preparation and properties of amorphous titania-coated zinc oxide nanoparticles," J. Solid State Chem. 179:2020-2026.
Liufu et al., 2004, "Investigation of PEG adsorption on the surface of zinc oxide nanoparticles," Power Technology 145:20-24.
Written Opinion in International Application No. PCT/US10/059156, mailed Mar. 21, 2013.

* cited by examiner

*Primary Examiner* — Brian-Yong Kwon
*Assistant Examiner* — Andrew S Rosenthal
(74) *Attorney, Agent, or Firm* — Anne Louise St. Martin

(57) ABSTRACT

Described herein are films comprising a zinc-containing compound and a film-stabilizing ingredient, for use in oral and personal care compositions.

16 Claims, No Drawings

ORAL AND PERSONAL CARE COMPOSITIONS

BACKGROUND

There is an ongoing need for stable oral and personal care compositions comprising films that are able to deliver effective amounts of zinc ions.

SUMMARY

Some embodiments of the present invention provide a film comprising a zinc-containing compound; one or more film forming polymers; and an effective amount of a film stabilizing ingredient. In some embodiments, the films are incorporated into oral and/or personal care compositions.

Other embodiments provide a method of increasing the stability of a film comprising a zinc-containing compound, comprising: mixing an effective amount of a film stabilizing ingredient with a zinc-containing compound; slurrying said mixture with one or more film forming polymers; and casting the slurry into a film.

Further embodiments include methods of treating a disease or condition of the oral cavity comprising administering a composition comprising a film as described herein and a carrier, to a subject in need thereof.

DETAILED DESCRIPTION

As used herein, "dentifrice" means a paste, gel, or liquid formulation. The dentifrice may be in any desired form, such as deep striped, surface striped, multi-layered, having a gel surround the paste, or any combinations thereof. The film contained in the oral care composition may be of any desired shape or structure, including multiple small strips, or one continuous strip.

In some embodiments, the present invention provides an orally acceptable zinc-containing film, comprising: a zinc-containing compound; one or more film forming polymers; and an effective amount of a film stabilizing ingredient.

In some embodiments, the zinc-containing compound is present in an amount greater than about 30% by weight of the film. In some embodiments, the film stabilizing ingredient is a charge stabilizing ingredient. In some embodiments, the film stabilizing ingredient is selected from the group consisting of polyethylene glycol (PEG), titanium dioxide and a mixture thereof. In some embodiments, the film stabilizing ingredient is PEG. In some embodiments, the PEG is PEG-600.

In other embodiments, the zinc-containing compound is present at a concentration of from about 30 to about 60% by weight, of the film. In further embodiments, the zinc-containing compound is present at a concentration of from about 40 to about 55% by weight, of the film. In yet further embodiments, the zinc-containing compound is present at a concentration of about 50% by weight, of the film.

In some embodiments, the zinc-containing compound is selected from the group consisting of: zinc oxide; zinc sulfate; zinc chloride; zinc citrate; zinc lactate; zinc gluconate; zinc malate; zinc tartrate; zinc carbonate; zinc phosphate; and a combination of two or more thereof. In some embodiments, the zinc-containing compound is zinc oxide or zinc citrate. In other embodiments, the zinc-containing compound is zinc oxide.

In some embodiments the film stabilizing ingredient is titanium dioxide. In some embodiments, the film stabilizing ingredient comprises a mixture of PEG and titanium dioxide.

In some embodiments, the film stabilizing ingredient and the zinc-containing compound are present in the film in a weight ratio of from about 1:2 to about 1:25. In some embodiments, the film stabilizing ingredient and the zinc-containing compound are present in the film in a weight ratio of from about 1:3 to about 1:20. In some embodiments, the film stabilizing ingredient and the zinc-containing compound are present in the film in a weight ratio of about 1:19. In some embodiments, the film stabilizing ingredient and the zinc-containing compound are present in the film in a weight ratio of about 1:18. In some embodiments, the film stabilizing ingredient and the zinc-containing compound are present in the film in a weight ratio of from about 1:4 to about 1:10. In some embodiments, the film stabilizing ingredient and the zinc-containing compound are present in the film in a weight ratio of about 1:4.

In some embodiments, the polyethylene glycol is present at a concentration of from about 5 to about 50% by weight. In other embodiments, the polyethylene glycol is present at a concentration of from about 10 to about 25% by weight. In other embodiments, the polyethylene glycol is present at a concentration of about 14% by weight. Yet other embodiments provide films wherein the titanium dioxide is present at a concentration of from about 0.01 to about 10% by weight, of the film. Still further embodiments provide films wherein the titanium dioxide is present at a concentration of from about 0.5 to about 5% by weight. Other embodiments provide films wherein the titanium dioxide is present at a concentration of about 4% by weight. Still other embodiments provide films wherein the titanium dioxide is present at a concentration of about 1% by weight.

In some embodiments, at least one of the one or more film forming polymers comprises one or more cellulose polymers. In some embodiments, at least one of said one or more cellulose polymers is a hydroxyalkyl methyl cellulose. In some embodiments, at least one of said one or more cellulose polymers is hydroxypropyl methyl cellulose.

Other embodiments provide an oral care composition comprising: any of the films described herein, and an orally acceptable carrier. In some embodiments, the film is in the form of flakes, fragments or strips.

In some embodiments, the film comprises from about 0.05% to about 5%, by weight, of the oral care composition. In other embodiments, the film comprises from about 0.1% to about 3%, by weight, of the oral care composition. In some embodiments, the film comprises about 0.15% by weight, of the oral care composition. In some embodiments, the film comprises about 0.2% by weight, of the oral care composition. Further embodiments provide compositions wherein the film comprises from about 0.5% to about 2% by weight, of the oral care composition.

In some embodiments, the zinc-containing compound comprises from about 0.5% to about 2.5%, by weight, of the oral care composition. In other embodiments, the zinc-containing compound comprises from about 1% to about 2%, by weight, of the oral care composition.

Still other embodiments provide methods of treating a disease or condition of the oral cavity comprising: contacting an oral cavity surface with any of the compositions described herein.

Other embodiments provide methods of increasing the stability of a zinc-containing film, comprising: mixing an effective amount of a film-stabilizing ingredient with a zinc-containing compound; slurrying the mixture of a film-stabilizing ingredient and a zinc-containing compound with one or more film forming polymers; and casting the slurry into a film. In some embodiments, the methods further comprise the step of cutting or punching the film to form film flakes, fragments or strips. In some embodiments, the casting of the film can be achieved by dispensing the slurry on a surface wherein the slurry forms a layer thereon and upon drying to remove solvent, produces a film. In some embodiments, the zinc-containing is pre-mixed with a film stabilizing ingredient, i.e., before being mixed with the other ingredients.

As referred to herein, an "oral or personal care composition" is any composition that is suitable for administration or application to a human or animal subject for enhancing the health, hygiene or appearance of the subject, including the prevention or treatment of any physiologic condition or disorder, and providing sensory, decorative or cosmetic benefits and combinations thereof.

In some embodiments, the film has a substantially lamellar structure. A "lamellar" structure has, or is capable of having, a size in one or two dimensions (e.g., the x- or y-dimensions) that is substantially greater than the thickness of the structure in a third dimension (e.g., the z-direction).

Film forming polymers useful herein include hydrophilic polymers and hydrophobic polymers. In certain embodiments, the polymer is a water soluble polymer. In some embodiments, the polymer is a water soluble, breakable polymer that dissolves during use, such as, for example, during tooth brushing. The dissolution can occur as a result of, for example, shearing and/or exposure to a solvent comprising a high concentration of water, such as saliva. In some embodiments, the polymer is insoluble but breakable in water by being dispersible, i.e., the polymer breaks down into small fragments, for example, as a result of shearing. In some embodiments, a polymer is insoluble but swellable. In configurations in which a polymer does not break down during use, the polymer can be a water-repellant polymer or an aqueous-stable hydrophilic polymer such as certain types of cellulose, for example paper.

Water soluble polymers among those useful herein include cellulose polymers, methacrylates, polyvinylpyrollidone, and mixtures thereof. In some embodiments, the cellulose polymer is selected from hydroxyalkyl cellulose polymers such as hydroxyalkyl methyl cellulose, hydroxypropyl methyl cellulose (HPMC), hydroxypropyl cellulose, hydroxyethyl cellulose, methyl cellulose, carboxymethyl cellulose, and mixtures thereof.

Other polymers among those useful herein include polyvinylpyrrolidone, cross-linked polyvinyl pyrrolidone, polyvinylpyrrolidone-vinyl acetate copolymer, polyvinylalcohol, polyacrylic acid, poly acrylate polymer, cross-linked polyacrylate polymer, cross-linked polyacrylic acid (e.g, Carbopol®), polyethylene oxide, polyethylene glycol, poly vinylalkyl ether-maleic acid copolymer (such as Gantrez®) and carboxy vinyl polymer; natural gums such as sodium alginate, carrageenan, xantham gum, gum acacia, arabic gum, guar gum, pullulan, agar, chitin, chitosan, pectin, karaya gum, zein, hordein, gliadin, locust bean gum, tragacanth and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan and gluten; and proteins such as collagen, whey protein isolate, casein, milk protein, soy protein and gelatin.

Non-limiting examples of water dispersable and swellable polymers include modified starch, alginate esters, divalent or multivalent ion salts of alginates. Non-limiting examples of water insoluble polymers include polymers soluble in at least one organic solvent, such as cellulose acetate, cellulose nitrate, ethylene-vinyl acetate copolymers, vinyl acetate homopolymer, ethyl cellulose, butyl cellulose, isopropyl cellulose, shellac, silicone polymer (e.g. dimethylsilicone), PMMA (poly methyl methacrylate), cellulose acetate phthalate and natural or synthetic rubber; polymers insoluble in organic solvents, such as cellulose, polyethylene, polypropylene, polyesters, polyurethane and nylon.

The films described herein can be made in accordance with the methods described in U.S. Pat. No. 6,669,929, and U.S. Patent Application Publication No. 2003/0053962.

In some embodiments, the film forming polymer comprises two different molecular weights of hydroxypropylmethylcellulose (HPMC) specifically, Methocel E5 and E50, commercially available from Dow Chemical, Midland, Mich.

In various embodiments, the size of the film flakes, fragments or strips may be determined pursuant to any of a variety of criteria, including manufacturing convenience, affect on visual appearance, surface area, affect on texture in the composition, and combinations thereof.

In various embodiments, the film may comprise, in addition to the zinc-containing compound, other therapeutic actives. As referred to herein, a therapeutic active is a material that is useful for the prevention or treatment of a physiological disorder or condition. Such disorders or conditions include, for example, those of the oral cavity (including the teeth and gingiva), skin, etc. The specific therapeutic active is preferably determined according to the desired utility of the composition.

In some further embodiments, the films further comprise one or more additional components such as diols, surfactants, starches, flavor agents, sweeteners, cationic prophylactic and therapeutic agents, fluoride ion sources, stannous ion sources, antioxidants, nutrients or proteins.

In some embodiments, the film or the oral care composition comprises an oral care active, which is useful for the prevention or treatment of an oral care disorder or condition. Oral care actives among those useful herein include abrasives, anticaries agents, tartar control agents, antiplaque agents, periodontal actives, breath freshening agents, malodor control agents, desensitizing agents, salivary stimulants, whitening agents, and combinations thereof. Oral care actives among those useful herein are described in U.S. Pat. No. 6,596,298 to Leung, et al.

In some embodiments, the zinc-containing compound is present in the form of particles. In some embodiments, the particles have an average particle size of about 1 to about 1000 nm. In other embodiments, the particles may have an average particle size from about 1 µm to about 850 nm, about 50 µm to about 150 nm, about 15 nm to about 500 nm, about 30 nm to about 250 nm and/or about 5 µm to about 100 nm.

Physical characteristics of the film containing the relatively high concentration of zinc-containing compounds can be modified by modifying various parameters of the film forming process.

In some embodiments, the films dissolve in the oral cavity of a subject. Dissolution time is the amount of time needed to dissolve a piece of film in a stagnant volume of water. Films having rapid dissolution times sometimes have low tensile strength because they are rapidly disintegrated. Characteristics of the film, such as tensile strength and dissolution time, therefore can be tailored during the formulation process based on the requirements of the final product. A person having ordinary skill in the art will appreciate that a balance exists between these two properties to specifically formulate a robust film that can withstand processing and still dissolve readily in the mouth.

The compositions of the embodiments may be described as comprising two phases, wherein one phase comprises a carrier and a second phase comprises the films described herein.

The term "phase" as used herein denotes a physical phase as understood in the physical and material sciences, i.e., a portion of a material whose properties and composition are uniform. However, a phase as used herein can be discontinuous, i.e., a phase can comprise a plurality of separate components. For example, a plurality of polymer film fragments of identical composition is considered to comprise a single phase. In some embodiments, a film fragment can be entirely embedded within the material comprising the first phase, or totally or partially exposed on the surface of the first phase. For example, if the composition is a dentifrice comprising both a gel and film fragments, a film fragment can be totally surrounded by the gel, or partially or totally exposed on the surface of the gel. In certain embodiments, compositions comprise more than two phases. Such multi-phase compositions include those having two carriers, each of which contributes a phase to the composition, in addition to film fragments as described herein. Other multi-phase compositions include those having a single carrier and two or more pluralities of fragments, wherein the pluralities of fragments have differing compositions.

In various embodiments, the carrier is a liquid, semi-solid or solid. A "liquid" can be a liquid of low or high viscosity. A liquid can be a liquid such that flow is imperceptible under ambient conditions. For example, a soap, such as an ordinary bar of hand soap, can be considered a liquid herein. A liquid can be a thixotropic liquid. A "semi-solid" as used herein can be a gel, a colloid, or a gum. As used herein, semi-solids and liquids are fluids distinguished on the basis of viscosity: a semi-solid is a high viscosity fluid, while a liquid has lower viscosity. There is no definitive dividing line between these two types of fluids. A semi-solid can, in certain embodiments, have a viscosity as high as thousands of mPa·s. Carriers among those useful herein include liquids, pastes, ointments, and gels, and can be transparent, translucent or opaque.

In certain embodiments, the compositions of the present invention are suitable for administration to the oral cavity. Such compositions include dentifrices, mouthwashes, dental gels, lozenges, beads, gums, oral strips, mints, liquid toothpastes, sprays, paint-on gels, lip balms, whitening strips, breath strips, oral chews, and combinations thereof. An oral care composition disclosed herein can be used, for example, for cavity prevention, whitening, plaque prevention or reduction, gingivitis prevention or reduction, tartar control, sensitivity prevention or reduction, or breath malodor prevention or reduction, and stain prevention.

The specific composition of the carrier preferably depends on the intended use of the composition. In various embodiments, the carrier is aqueous, comprising from about 5% to about 95% water or from about 10% to about 70% water. In other embodiments, the carrier is substantially non-aqueous. In a dentifrice carrier, water content can be from about 5% to about 70%, from about 10% to about 50%, or from about 20% to about 40%. When the presence of water will cause the film to disintegrate, it is particularly preferred that the dried film contain no free water, in which the amount of water is less than 1%. In some embodiments, the amount of water is negligible.

The carrier may comprise any of a variety of materials, including emulsifiers, thickeners, fillers, and preservatives. In some embodiments, the carrier may include a functional or active material, such as those described above. In some embodiments, the carrier comprises the same functional material as the film.

In one embodiment, the carrier is suitable for use as a dentifrice. Carrier compositions among those useful herein are disclosed in U.S. Pat. Nos. 5,695,746 to Garlick, Jr., et al. and 4,839,157 to Mei-King Ng, et al.

In various dentifrice embodiments, the carrier comprises thickeners, gelling agents or combinations thereof. Thickeners or gelling agents useful herein include inorganic, natural or synthetic thickeners or gelling agents. In some configurations, the carrier comprises the thickener and gelling agent at total levels of from about 0.1% to about 15%, by weight, or from about 0.4% to about 10% by weight of the composition. Examples of thickeners and gelling agents useful herein include inorganic thickening silicas such as: amorphous silica, for example Zeodent® 165 (Huber Corporation); Irish moss; iota-carrageenan; gum tragacanth; or polyvinylpyrrolidone. In certain embodiments, the carrier comprises a polishing agent, such as a silica, a calcined alumina, sodium bicarbonate, calcium carbonate, dicalcium phosphate or calcium pyrophosphate. In various embodiments, the carrier can be a visually clear composition.

In various dentifrice embodiments, comprising a visually clear carrier, the composition comprises at least one polishing agent. Polishing agents among those useful herein include collodial silica, such as, for example, Zeodent® 115 (Huber Corporation), and alkali metal aluminosilicate complexes (i.e., a silica comprising alumina). In some configurations, a polishing agent can have a refractive index close to that of a gelling agent combined with water and/or humectant. In various embodiments, the carrier comprises the polishing agent at a level of from about 5% to about 70% by weight of the composition.

In certain dentifrices, the carrier comprises a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments the carrier comprises the surfactant at a level of from about 0.3% to about 5% by weight of composition, or about 0.5% to about 3% by weight of composition.

In various embodiments the compositions described herein are stable upon storage at ambient temperature for at least about two years. It is understood, however, that in some embodiments, an otherwise stable film can disintegrate during use (as discussed above), for example, during toothbrushing using a dentifrice composition.

The embodiments also provide processes for making compositions comprising a film as described herein; and a carrier. In various embodiments, a plurality of film fragments are combined with a carrier. In some embodiments, a carrier and a plurality of film fragments can be mixed. In some embodiments, the mixing can comprise slow stirring. In some embodiments, the process for making the composition comprising a carrier having distributed therein a plurality of lamellar fragments includes: providing the carrier; adding lamellar fragments of a film prepared as described herein, i.e. containing a zinc-containing compound, one or more film forming polymers, and an effective amount of a film-stabilizing ingredient to the carrier to form a mixture; and homogenizing the mixture.

The term "homogenizing" as used herein refers to the admixture of the fragments and the carrier so as to attain a substantially homogeneous distribution of fragments in the carrier. In some embodiments, the resulting composition still retains two-phase composition characteristics.

Certain embodiments described herein also provide methods for administering a zinc-containing compound in order treat a disease or condition of the oral cavity. The film or composition containing the same is administered to a human or animal subject. In various embodiments, the administration is topical, wherein the composition is applied to an external surface of the subject, such as to a surface of the oral cavity (e.g., teeth, gingiva, and tongue). The specific route and method of administration will depend, of course, on the intended use of the composition. In some embodiments, the disease or condition is selected from caries, gingivitis, periodontitis, and cosmetic conditions such as yellowing and malodor.

In some embodiments, the methods additionally comprise disrupting the film after topically applying the film. Such disruption may be accomplished by any of a variety of methods, including chemical and/or mechanical means. Chemical means include degradation of the film by contact with water or a material present at the site of administration (e.g., saliva in an oral care application). Physical means include agitation, grinding, and shear forces produced by application of physical energy to the composition during use (e.g., brushing in a dentifrice application).

The present inventors found, quite unexpectedly, that when using zinc-containing compounds such as zinc oxide in a film, the stability of the film can be enhanced by including a film-stabilizing ingredient. In some embodiments, the film-stabilizing ingredient has the ability to interact with the zinc-containing compound in the film, e.g. zinc oxide, thereby decreasing its positive surface charge and thus stabilize the film.

It will be understood by those of ordinary skill in the art that further aspects of the invention include films containing a film-stabilizing ingredient and/or charge stabilizing ingredient besides those mentioned above. Any such art recognized film-stabilizing ingredient will be suitable for inclusion in the compositions and films described herein. The amount that these alternative film-stabilizing ingredients are included in the films of the present invention is generally described herein functionally, i.e. an effective amount. The actual amount, however, will vary depending upon the film-stabilizing ingredient selected. The amount (calculated on a weight basis) for any film-stabilizing ingredient or combination thereof may be but is not necessarily the same as those weight ranges provided above with respect to the PEG or $TiO_2$. Such amounts are ascertainable by those skilled in the art.

The embodiments described herein can be further understood by reference to the following non-limiting examples.

EXAMPLES

Example 1

Table 1 (below) describes the formulations of five (5) films. Film X serves as a control. During the manufacture of Films B and D, a film stabilizing ingredient was mixed with the zinc oxide prior to addition to the slurry of film forming polymers.

TABLE 1

| Film | X w/w % | A w/w % | B w/w % | C w/w % | D w/w % |
|---|---|---|---|---|---|
| HPMC E5 | 17.81 | 16.63 | 16.88 | 14.67 | 13.64 |
| HPMC E50 | 15.83 | 15.12 | 15.25 | 13.59 | 14.96 |
| ZnO | 48.01 | 50.45 | 50 | 51.63 | 49.86 |
| Propylene Glycol | 14.11 | — | — | 12.24 | — |
| Polyethylene Glycol | — | 13.9 | 13.65 | — | 13.39 |
| Polysorbate 80 | 0.9 | 0.9 | 0.96 | 0.82 | 0.79 |
| $TiO_2$ | — | — | — | 4.07 | 4.21 |
| Menthol | 3.38 | 3.01 | 3.26 | 2.99 | 3.14 |

Example 2

This Example describes a method for preparing films of the instant invention. Zinc oxide and the film-stabilizing ingredient are mixed. A slurry is prepared by heating deionized water to about 80° C. About half of the formula amount of water is added to beaker. HPMC E5 is then added and mixed with an overhead mixer until the polymer is wet. HPMC E50 is then added and the slurry is mixed for 20 min with intermittent scraping of the beaker walls to ensure polymer incorporation. The zinc oxide and film-stabilizing ingredient mixture is then added to the slurry along with the remaining amount of water. The slurry is then mixed for 20 minutes. Air bubbles in the slurries can be removed by mixing with the SpeedMixer™ DAC 150 FVZ for 5 min at 1800 rpm. The slurry is then dispensed on surface and dried to produce a film. The film can by punched into flakes, fragments or strips as desired.

Example 3

The films described in Example 1 were immersed for 15 days in a simple slurry containing sorbitol, water, SLS, betaine, saccharin, fluoride, PEG, and sodium phosphate (dibasic) at pH 6.8. The films were then filtered and the total zinc concentration in the slurries was analyzed. The results of this 15-day test are described in Table 2 (below).

TABLE 2

|  | X | A | B | C | D |
|---|---|---|---|---|---|
| Total Zn (ppm) | 1.23 | 1.16 | 1.01 | 1.23 | 1.14 |

Example 4

Slurries with titanium dioxide ("E") and without titanium dioxide ("Y") were prepared (see, Table 3 below).

TABLE 3

| Ingredient | Y | E |
|---|---|---|
| Water | 62.35 | 61.35 |
| Methocel E5 | 6.25 | 6.25 |
| Methocel E50 | 5.64 | 5.64 |
| Zinc oxide | 18.66 | 18.66 |
| Titanium dioxide | — | 1 |
| Ethanol | 5.56 | 5.56 |
| Methol | 1.23 | 1.23 |
| Tween 80 | 0.31 | 0.31 |

The slurries were then cast with a 15 mil casting bar onto a plastic substrate and then dried for 15 minutes at 105° C. The resultant film was ground into film particles of 12 to 20 meshes. Additional slurries comprising 50 parts propylene glycol, 49.85 parts MaxFresh Night Toothpaste (see, Table 4 below) and 0.15 parts of film particles, were then prepared.

TABLE 4

| Ingredient | w/w % |
| --- | --- |
| Polyethylene glycol | 1 |
| Carboxymethyl cellulose | 0.55 |
| Sodium saccharin | 0.35 |
| Sodium fluoride | 0.32 |
| Sorbitol (70% solution) | 68 |
| Water | 9.05 |
| Colorant | 0.01 |
| Zeodent 114 | 8 |
| Zeodent 165 | 8 |
| Cocamidopropyl betaine | 1.25 |
| Sodium lauryl sulfate | 1.57 |
| Flavor | 1.40 |

The slurries were ultrasonicated for six hours to accelerate zinc oxide migration. The temperature was controlled at 23° C. by circulating tap water. The film particles were removed from the slurries using a 40 mesh sieve. Five percent nitric acid solution was used to dilute the filtered slurries and convert the zinc oxide to soluble zinc ion. The level of zinc in the diluted solution was quantified by atomic absorption. Results of the two comparative trials that were conducted, are described below in Table 5.

TABLE 5

| Film | Trial | Quantity of zinc in diluted solution (ppm) | % Reduction |
| --- | --- | --- | --- |
| Y | 1 | 47.65 | — |
| E | 1 | 30.46 | 36.1 |
| Y | 2 | 44.79 | — |
| E | 2 | 28.32 | 36.8 |

The data described in Table 5 (above) indicates that migration of the zinc-containing compound was significantly reduced in the films containing titanium dioxide.

Each of the patents, patent applications and printed publications (including books) mentioned in this document are hereby incorporated by reference in their entirety.

As those skilled in the art will appreciate, numerous changes and modifications may be made to the embodiments described herein without departing from the spirit of the invention. It is intended that all such variations fall within the scope of the appended claims.

What is claimed is:

1. An orally acceptable zinc-containing film, comprising:
a zinc-containing compound;
one or more film forming polymers; and
an effective amount of a film stabilizing ingredient,
wherein the film stabilizing ingredient is a charge stabilizing ingredient selected from the group consisting of polyethylene glycol, titanium dioxide, and a mixture thereof;
wherein the zinc-containing compound is present at a concentration of from about 30 to about 60% by weight; and
wherein said zinc-containing compound is selected from the group consisting of: zinc oxide; zinc sulfate; zinc chloride; zinc citrate; zinc lactate; zinc gluconate; zinc malate; zinc tartrate; zinc carbonate; zinc phosphate; and a combination of two or more thereof.

2. The film of claim 1, wherein the zinc-containing compound is present at a concentration of from about 40 to about 55% by weight.

3. The film of claim 1, wherein said zinc-containing compound is zinc oxide or zinc citrate.

4. The film of claim 1, wherein the film stabilizing ingredient is polyethylene glycol or titanium dioxide.

5. The film of claim 1, wherein at least one of said one or more film forming polymers is a cellulose polymer.

6. The film of claim 1, wherein the cellulose polymer is a hydroxyalkyl methyl cellulose.

7. The film of claim 1, wherein the zinc containing compound is zinc oxide, the film stabilizing ingredient is polyethylene glycol or titanium dioxide, and the cellulose polymer is hydroxypropyl methyl cellulose.

8. An oral care composition comprising:
the film of claim 1; and
an orally acceptable carrier.

9. A method of increasing the stability of an orally acceptable zinc-containing film, comprising:
a) mixing an effective amount of a film stabilizing ingredient with a zinc-containing compound to form a mixture;
b) slurrying the mixture of step a) with one or more film forming polymers to form a slurry; and
c) casting the slurry into a film,
wherein the film comprises about 30 to about 60% by weight of the zinc-containing compound, and wherein the film stabilizing ingredient is selected from the group consisting of polyethylene glycol, titanium dioxide, and a mixture thereof.

10. The method of claim 9, wherein the film stabilizing ingredient is a charge stabilizing ingredient.

11. The method of claim 9, further comprising the step of cutting or punching the film to form film flakes, fragments or strips.

12. The film of claim 2, wherein said zinc-containing compound is selected from the group consisting of: zinc oxide; zinc chloride; zinc citrate; zinc phosphate; and a combination of two or more thereof.

13. The film of claim 12, wherein at least one of said one or more film forming polymers is a cellulose polymer.

14. The film of claim 13, wherein the cellulose polymer is a hydroxyalkyl methyl cellulose.

15. The film of claim 14, wherein said zinc-containing compound is zinc oxide or zinc citrate.

16. The film of claim 15, wherein the zinc containing compound is zinc oxide, the film stabilizing ingredient is polyethylene glycol or titanium dioxide, and the cellulose polymer is hydroxypropyl methyl cellulose.

* * * * *